(12) United States Patent
Dalgleish et al.

(10) Patent No.: US 11,885,796 B2
(45) Date of Patent: Jan. 30, 2024

(54) ASSAY TO IDENTIFY ANTI-CANCER AGENTS

(71) Applicant: LDN Pharma Limited, England (GB)

(72) Inventors: Angus Dalgleish, London Greater London (GB); Wai Lui, London Greater London (GB)

(73) Assignee: LDN Pharma Ltd., London (GB)

( * ) Notice: Subject to any disclaimer, the term of this patent is extended or adjusted under 35 U.S.C. 154(b) by 967 days.

(21) Appl. No.: 16/498,373

(22) PCT Filed: Mar. 28, 2018

(86) PCT No.: PCT/GB2018/050828
§ 371 (c)(1),
(2) Date: Sep. 26, 2019

(87) PCT Pub. No.: WO2018/178675
PCT Pub. Date: Oct. 4, 2018

(65) Prior Publication Data
US 2020/0110070 A1    Apr. 9, 2020

(30) Foreign Application Priority Data
Mar. 28, 2017 (GB) ...................... 1704913

(51) Int. Cl.
*G01N 33/50* (2006.01)
*A61K 31/485* (2006.01)
*A61P 35/00* (2006.01)

(52) U.S. Cl.
CPC ........ *G01N 33/5011* (2013.01); *A61K 31/485* (2013.01); *A61P 35/00* (2018.01); *G01N 33/5008* (2013.01)

(58) Field of Classification Search
CPC .... G01N 33/5011; A61P 35/00; A61K 31/485
See application file for complete search history.

(56) References Cited

U.S. PATENT DOCUMENTS

2010/0286059 A1* 11/2010 Moss ................. G01N 33/5011
514/19.3

FOREIGN PATENT DOCUMENTS

WO    2015/189597 A1    12/2015

OTHER PUBLICATIONS

Wang et al. "Methylnaltrexone, a peripherally acting opioid receptor antagonist, enhances tumoricidal effects of 5-Fu on human carcinoma cells," Anticancer. Res. Aug. 2009;29(8):2927-32. PMID: 19661297. (Year: 2009).*
Suzuki et al., "Peripheral opioid antagonist enhances the effect of anti-tumor drug by blocking a cell growth-suppressive pathway in vivo," PLoS One Apr. 8, 2015;10(4):e0123407. PMID: 25853862. (Year: 2015).*
Donahue et al., "Los-dose naltrexone suppresses ovarian cancer and exhibits enhanced inhibition in combination with cisplatin," Exp. Biol. and Medicine, 236(7):883-895, 2011.
Liu et al., "Naltrexone at low doses upregulates a unique gene expression not seen with normal doses: Implications for its use in cancer therapy," Int'l. J. of Oncol., 49(2):793-802, Aug. 2016.
Jenkins, Gareth, Written Opinion of the International Searching Authority, PCT/GB2018/050828, European Patent Office, dated Jun. 15, 2018.
Singleton et al., "Synergistic effects of methylnaltrexone with 5-fluorouracil and bevacizumab on inhibition of vascular endothelial growth factor-induced angiogenesis," Mol. Cancer Ther., 7(6):1669-1679, Jun. 2008.

* cited by examiner

*Primary Examiner* — Theodore R. Howell
(74) *Attorney, Agent, or Firm* — Gavrilovich, Dodd & Lindsey LLP

(57) ABSTRACT

An in vitro method for identifying an anti-cancer agent, the therapeutic efficacy of which is enhanced upon administration with a second agent that increases the expression of OPRK1 and/or BAD, comprising the steps of:
  a. co-incubating a population of cells with a target anti-cancer agent and said second agent and
  b. measuring the cytotoxicity and/or cytostasis in the population of cells;
     wherein the therapeutic efficacy of the target anti-cancer agent is enhanced if the cytotoxicity and/or cytostasis of the target anti-cancer agent is increased compared to a control.

12 Claims, 5 Drawing Sheets

ASSAY TO IDENTIFY ANTI-CANCER AGENTS

CROSS REFERENCE TO RELATED APPLICATIONS

This application is a U.S. National Stage Application filed under 35 U.S.C. § 371 and claims priority from International Application No. PCT/GB2018/050828, filed Mar. 28, 2019, which application claims the benefit of Great Britain Application No. 1704913.1, filed Mar. 28, 2017, the disclosures of which are incorporated herein in their entirety by reference.

FIELD OF THE INVENTION

This invention relates to an in vitro screening method for identifying anti-cancer agents that when co-administered alongside a second sensitising agent exhibits an increased therapeutic efficacy.

BACKGROUND OF THE INVENTION

The field of cancer therapeutics is currently undergoing a paradigm shift, with thanks to the advent of personalised medicine. Recent technological advances have made it easier than ever to genotype cancers and thus enable the administration of the most appropriate remedy for combating the particular strain of disease. For instance, personalised medicine enables a cancer characterised by a particular oncogenic mutation to be treated with an anti-cancer agent that directly or indirectly targets that particular oncogene. This strategy undoubtedly increases the chances of therapeutic success whilst simultaneously limiting the unnecessary exposure of the subject to aggressive treatment regimens that are often accompanied by side effects that significantly impair quality of life.

Personalised medicine is made possible by the increasing understanding of the different pathological mechanisms that underlie many types of cancers. Coupled to this is the increasing sophistication of anti-cancer therapies, which are largely borne out of the emerging understanding of the role of the immune system in the development and elimination of cancer.

It is now acknowledged that through a process of natural selection occult cancer cells can subvert recognition by the immune system and thus evade elimination during the earliest stages of tumour formation. The uncontrolled proliferation of immune-silent cancer cells also enables the generation of a tumour microenvironment that can inhibit additional arms of the immune system and create an environment optimal for further cancer growth, evasion, and metastasis.

Accordingly, some of the most successful anti-cancer therapies to have emerged on to the market in recent times are those that overcome the barrier to immune activation present within the tumour microenvironment.

Nevertheless, not all cancers are amenable to treatment by immunotherapy. As such, there is a need to continue developing and refining treatments involving more traditional anti-cancer agents such as chemotherapeutics. This must either be achieved by developing new anti-cancer therapeutics, or finding novel ways of boosting the therapeutic efficacy of existing anti-cancer agents.

SUMMARY OF THE INVENTION

The present invention is based on the discovery that agents that increase the expression of Opioid receptor kappa-1 (OPRK1) and/or Bcl-2 associated death promoter (BAD) boost the cytotoxicity of anti-cancer agents in cancer cells. The effect is exemplified in the present examples, which show that administration of said agents in an amount sufficient to increase the expression of OPRK1 by at least 5%, or at least 20% depending on the cancer cell type, and/or increase the expression of BAD by at least 10% depending on the cancer cell type, compared to normal basal levels within the cell, can result in an increase in the efficacy of an anti-cancer agent by up to 50%. Therefore, the present inventors have devised an in vitro method for screening for anti-cancer agents that would benefit from concurrent administration with a second agent that increases the expression of OPRK1 and/or BAD within the cancer cell.

According to a first aspect of the invention, there is provided a method for identifying an anti-cancer agent, the therapeutic efficacy of which is enhanced upon administration with a second agent that increases the expression of OPRK1 and/or BAD, comprising the steps of: (a) co-incubating a population of cells with a target anti-cancer agent and said second agent; and (b) measuring the cytotoxicity and/or cytostasis in the population of cells; wherein the therapeutic efficacy of the target anti-cancer agent is enhanced if the cytotoxicity and/or cytostasis of the target anti-cancer agent is increased compared to a control.

According to a second aspect of the invention, there is provided an in vitro method for determining the anti-cancer efficacy of a target agent, comprising the steps of: (a) incubating a population of cells with the target agent and a second agent that increases the expression of OPRK1 and/or BAD; (b) measuring the cytotoxicity and/or cytostasis in the population of cells; and (c) determining whether there is increased cytotoxicity and/or cytostasis compared to a control.

DESCRIPTION OF THE DRAWINGS

The invention is further defined by reference to the following drawings, in which.

DETAILED DESCRIPTION OF THE INVENTION

Figure 1A:
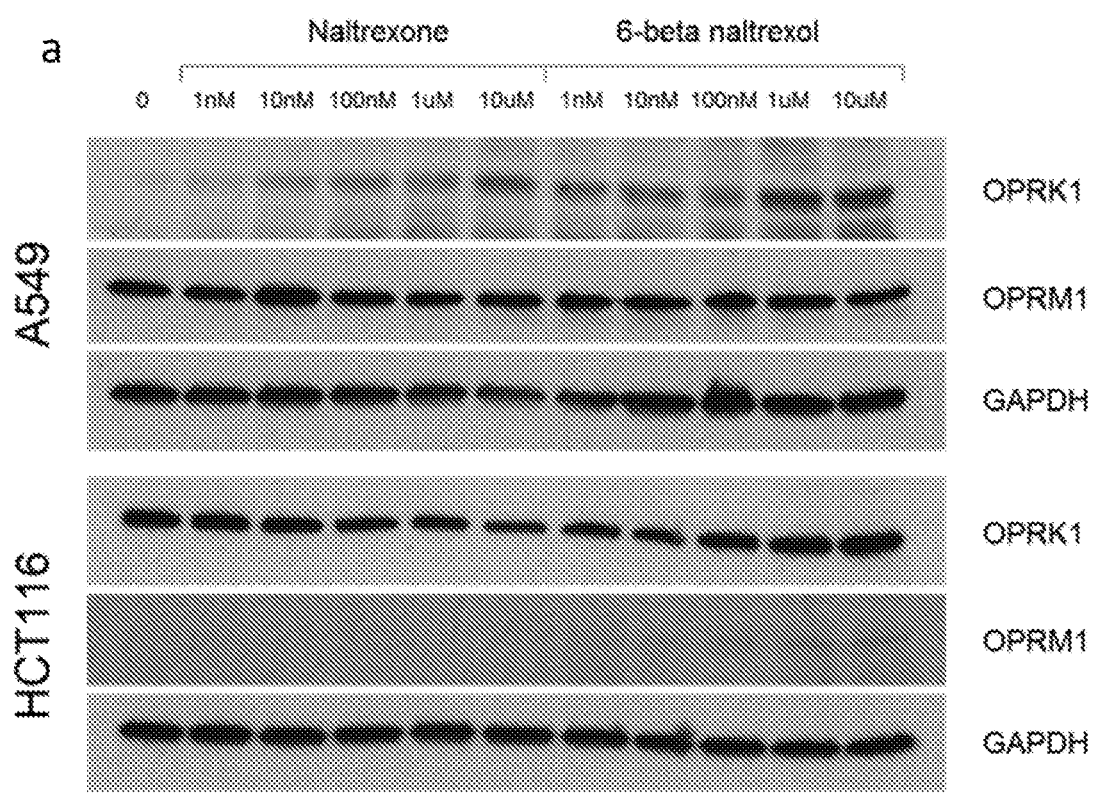
FIG. 1 shows the effect of increasing concentrations of 6-β-naltrexol and naltrexone on the expression of OPRK1, OPRM1, and GAPDH in A549 and HCT116 cells.
Figure 1B:
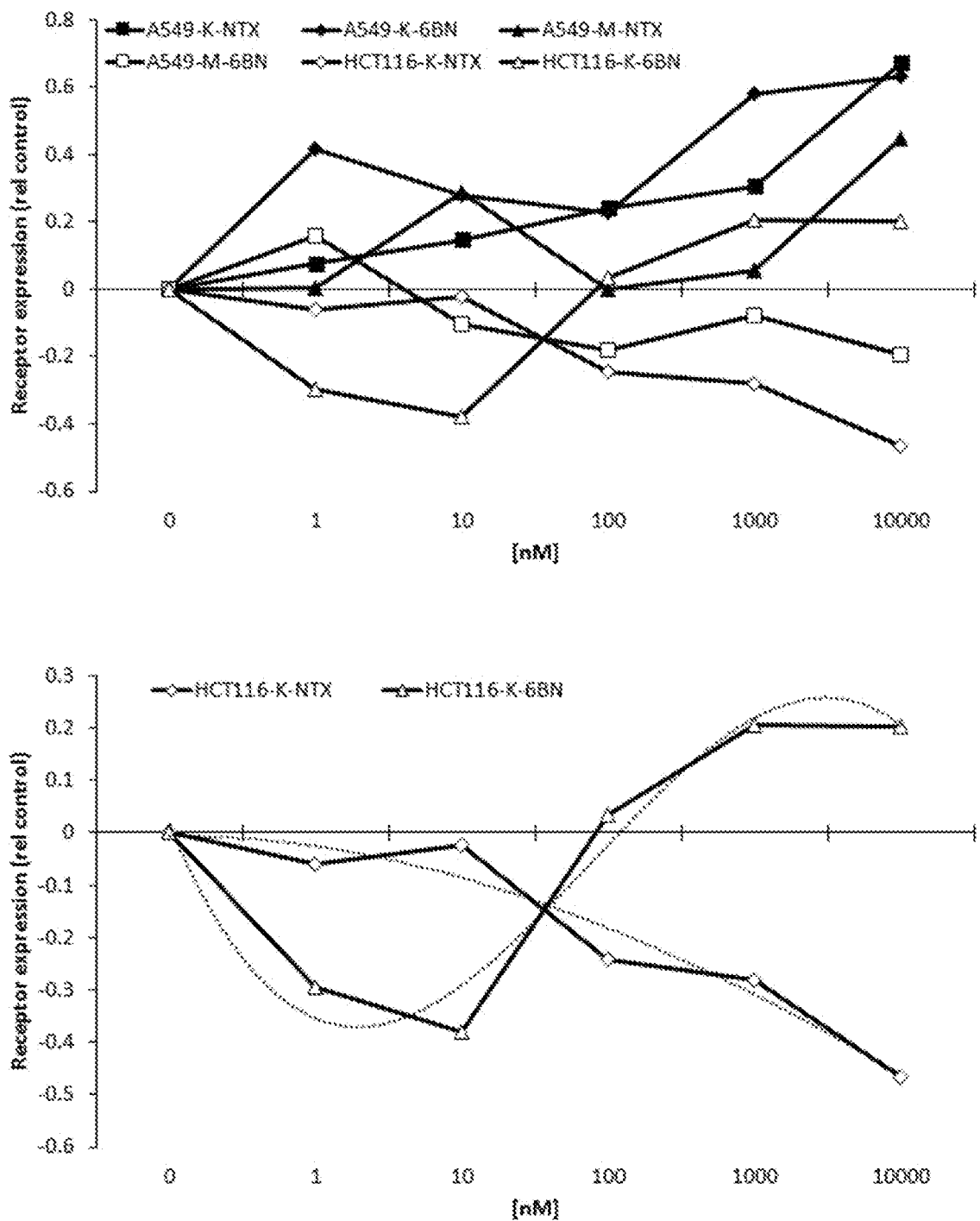

The present invention makes use of an agent that increases the expression of OPRK1 and/or BAD to enhance the therapeutic efficacy of an anti-cancer molecule. Such agents themselves display minimal cytotoxicity or cytostatic activity when administered to cancer cells, but enhance the cytotoxicity or cytostatic activity of the anti-cancer agents with which they are co-administered. Importantly, not all anti-cancer agents appear to benefit from concurrent administration alongside an agent that increases the expression of OPRK1 and/or BAD. Thus, the present invention provides a method of screening for anti-cancer agents that would experience a boost in therapeutic efficacy when co-administered alongside the agent that increases the expression of OPRK1 and/or BAD.

Without wishing to be bound by the theory, the increase in the expression levels of OPRK1 and/or BAD is an indication that the cell is sensitized to the effect of certain anti-cancer agents. OPRK1 and/or BAD are therefore useful markers for identifying anti-cancer agents that may show increased therapeutic efficacy when administered in combination with agents that increase expression of OPRK1 and/or BAD in a subject.

As used herein "sensitized" refers to the increased susceptibility of the cancer cell to cytotoxicity or cytostasis in response to administration of an anti-cancer agent, whereby the increased "sensitivity" is due to an increase in the level of expression of OPRK1 and/or BAD relative to a control.

In certain embodiments, the second agent is provided in an amount sufficient to increase the concentration of OPRK1 above the normal basal levels expected in the specific cancer cell type. For example, the agent may be administered in an amount sufficient to raise the level of expression of OPRK1 by at least 5%, at least 10%, at least 20%, at least 30%, at least 40%, at least 50%, at least 60%, 70%, at least 80%, at least 90%, or at least 100%, compared to the normal basal levels expected in the specific cancer cell type. The "normal" basal level may be determined by measuring the level of expression of OPRK1 in the cells prior to the administration of the second agent.

Furthermore, or in a separate embodiment, the second agent is provided in an amount sufficient to increase the concentration of BAD above the normal basal levels expected in the specific cancer cell type. For example, the agent may be administered in an amount sufficient to raise the level of expression of BAD by at least 5%, at least 10%, at least 20%, at least 30%, at least 40%, at least 50%, at least 60%, 70%, at least 80%, at least 90%, or at least 100%, compared to the normal basal levels expected in the specific cancer cell type. The "normal" basal level may be determined by measuring the level of expression of BAD in the cells prior to the administration of the second agent.

The level of expression of OPRK1 and/or BAD can be measured in the population of cells using any number of analytical methods available to the skilled person, including, but not limited to, gel electrophoresis and Western blot analysis, 2D-PAGE, column chromatography, ribosome profiling or mass spectrometry. The increased level of expression can be determined by comparing the level of expression of the biomarker from before or after administration of the agent that increases the level of expression of OPRK1 and/or BAD. The level of expression of the biomarker prior to administration of the second agent may be referred to as the normal basal level. Thus, the amount sufficient to raise the level of expression of OPRK1 and/or BAD by at least 5%, at least 10%, at least 20%, at least 30%, at least 40%, at least 50%, at least 60%, 70%, at least 80%, at least 90%, or at least 100% compared to basal levels can be determined by comparing the level of expression of OPRK1 and/or BAD before and after the administration of a particular amount of the second agent. In certain embodiments, the desired amount is sufficient to raise the level of expression of OPRK1 and/or BAD by at least 20% and and least 10% respectively.

As used herein, "control" refers to a reference value to which the cytotoxicity or cytostasis of the target agent when administered in combination with the second agent is to be compared. For example, the reference value may be the cytotoxicity or cytostasis of a population of cells administered the target agent, only in (i.e. the absence of the second agent). The measurement of the control may be incorporated into the method of the invention, for example, by including a population of cells that are to be administered only the target agent.

Alternatively, the control may be a pre-approved value or a previously calculated value derived from a previous iteration of the method of the invention. In some instances, the control may be the sum of the cytotoxic or cytostatic effects of both the target agent and the second agent administered independently. In certain embodiments, the cytotoxicity or cytostasis is enhanced when cytotoxicity or cytostasis is increased by at least 10%, at least 20%, at least 30%, at least 40%, at least 50%, at least 60%, at least 70%, at least 80%, at least 90%, at least 100%, compared to a control.

As used herein, "cytotoxicity" refers to the quality of an agent being toxic to cells. Cytotoxicity may therefore refer to the ability on an agent to induce cell death upon coming in to contact with a cell. The cytotoxic mechanism leading to cell death may be due to necrosis or programmed cell death (apoptosis). Cytotoxicity may be measured in a population of cells using any number of cell viability assays, or by using antibodies specific for protein factors activated upon the initiation of apoptosis. For the purposes of the present invention, a cell viability assay may be particularly desirable for enabling the measurement of cytotoxicity of multiple target agents simultaneously. Examples of the types of assays that can be employed in the method include, for example, assays that measure cytolysis or membrane leakage (such as propidium iodide or Trypan blue assays), assays that measure mitochondrial or metabolic activity (such as— (4,5-dimethylthiazol-2-yl)-2,5-diphenyltetrazolium bromide (MTT) assays), assays that measure caspase activity (using CellEvent Caspase-3/7 Green Detection Reagent (ThermoFisher), or assays that measure ATP levels (ApoSENSOR™ Cell Viability Assay Kit (Biovision)). Many commercially available kits utilize colorimetric readouts to determine the level of cytotoxicity within the cell sample. The colourimetric readout can be measured using conventional spectroscopic techniques by recording the absorbance or emission of light at particular wavelengths. The exact parameters of the cytotoxicity assay will be well known to the person skilled in the art and will vary depending on the type of assay used.

As used herein, "cytostasis" refers to the inhibition of cell growth and multiplication. Thus, a cytostatic agent may refer to an agent that inhibits the proliferation or growth of a cell, perhaps without causing cytotoxicity. An agent that causes cytostasis can be determined by measuring the DNA content of individual cells within a population of cells. A population of cells undergoing proliferation will have sub-populations of cells with varying levels of DNA content. The DNA content within the cell will be dependent on the phase of the cell cycle within which the cell resides. Where an agent causes cytostasis, the balance of the population of cells within each phase of the cell cycle will be abnormal. For example, if cytostasis occurs in the S phase or $G_2$ phase, an abnormal number of cells will contain twice the content of DNA normally observed in a somatic cell. Conversely, if cytostasis occurs during the $G_0$ or $G_1$ phase, an abnormal number of cells will contain the amount of DNA typically observed in a somatic cell.

As used herein, a "population of cells" refers to an in vitro cell culture to which the agents are to be administered for the purposes of the invention. Methods, techniques and conditions for culturing cells in vitro are well known to the person skilled in the art, and the exact culturing protocol will vary depending of the identity of the cells to be cultured. The cells may also be cultured in a variety of different formats depending on the number of agents that are to undergo the method of the invention simultaneously. For example, cells may be cultured in vitro in 6-well dishes, 12-well-dishes, 24-well dishes, 96-well dishes, or 128-well dishes and the like. The skilled person would be able to adjust the cell-seeding density appropriately in light of the type of cell to be used or in light of the chosen format in which the method is to be carried out, particularly as different types of cells proliferate at different rates. The skilled person would thus be aware of the need to perform a small degree of trial and error in order to arrive at the optimum set of conditions for maximising the effectiveness of the method.

The cells for use in the invention may be, or may be derived from, an immortalised cell line. An "immortalised" cell line refers to a population of cells that due to mutation undergo indefinite proliferation and evade normal cellular senescence. For example the cells may be, or may be derived from, SH-SY5Y, Hep-G2, HEK 293, RAW 264.7, HeLa, MRC-5, A2780, CACO-2, THP 1, A549, PD 30, MCF7, SNL 76/7, C2C12, Jurkat E6.1, U937, L929, 3T3 L1, HL60, PC-12, HT29, OE33, OE19, NIH 3T3, MDA-MB-231, K562, U-87 MG, PD-25, A2780cis, B9, CHO-K1, MDCK, 1321N1, A431, ATDC5, HUVEC, Vero, Fao, J774A.1, MC3T3-E1, J774.2, PNT1A, U-2 OS, HCT 116, MA104, BEAS-2B, NB2-11, BHK 21, NS0, Neuro 2a, T47D, 1301, PNT2, PC-3, TF1, COS-7, MDCK, NCI-322, SK,N.SH, LNCaP.FGC, OE21, PSN1, ISHIKAWA, MFE-280, MG-63, RK 13, EoL-1 cell, VCaP, tsA201, CHO, HT 1080, PANC-1, Saos-2, SK-OV-3, COV434, Hep 3B, A375, AGS, CAKI 2, COLO 205, COR-L23, IMR 32, QT 35, WI 38, HMVII, HT55, or TK6 cells. Preferably the cell line is chosen based on characteristics of the type of cancer that the second agent is commonly used to treat or has been developed to treat. For example, where the second agent is commonly used to treat pancreatic cancer in humans, an immortalised cancer line of human pancreatic cancer origin may be used in the method. Alternatively, where the second agent is an anti-cancer agent targeted towards a specific oncogene, the cell line chosen is one within which the oncogene-of-interest is essential for the viability of the cell line. Alternatively still, where no immortalised cell line exists due to the presence of a specific oncogene, any cell line may be engineered to express the oncogene-of-interest. Techniques for the modification of the genetic identity of immortalised cell lines are routine and well known to the skilled artisan. Such methods may be found in the following references, which are hereby incorporated in their entirety: Kim T K, Eberwine J H. Mammalian cell transfection: the present and the future. Anal Bioanal Chem. 2010 August; 397(8):3173-8. Alternatively, the method of the invention may use cells obtained directly from a subject having cancer. The cells may be obtained from a tumour biopsy from the subject, where the cells derived from the tumour sample are subsequently cultured in vitro. Preferably, the cells obtained from the subject are obtained from a tissue sample of the tumour. Methods for the extraction of a tumour sample and the subsequent culturing of the cells in vitro will be well known to the skilled person.

In certain embodiments, the population of cells are, or are derived from, an immortalised cell line. Preferably, the immortalised cell line is of human origin.

As used herein, "therapeutic efficacy" refers to the effectiveness of an agent for use in the treatment of a particular disease. The therapeutic efficacy of an agent may be specific for the treatment of one particular characteristic or symptom of a particular disease, particularly where the disease is multifactorial. In the context of cancer, the therapeutic efficacy may refer to the ability of an agent to prevent, reduce, alleviate, or halt the progression of symptoms of cancer. Thus, the therapeutic efficacy of an agent may be enhanced by providing a greater reduction, prevention or alleviation of one, several, or all symptoms of a disease than what would normally be expected when a particular dosage of the second agent is administered in the absence of the adjuvant-like molecule. What would "normally" be expected would be that observed in the normal course of treatment of a disease, for example the average reduction in tumour size upon administration of a particular dose of a particular anti-cancer agent, or the anticipated reduction in metastasis of a tumour upon administration of a routine dose of a particular anti-cancer agent. For the purposes of the present invention, the therapeutic efficacy of a target anti-cancer agent is said to be enhanced when the measured cytotoxicity or cytostasis is increased in the population of cells when the target agent is co-administered alongside the agent that increases the expression of OPRK1 and/or BAD in comparison to a control.

As used herein, the "target agent" or "target anti-cancer agent" refers to the agent under investigation according to the method of the invention. The "target" agent may be any compound known to have anti-cancer activity or any compound suspected of having anti-cancer activity. The compound may also be any agent yet to be identified as an anti-cancer agent. Preferably, the agent is a compound with known anti-cancer activity. Preferably, the agent is a compound with known chemotherapeutic activity.

As used herein "chemotherapy" and "chemotherapeutic" have their conventional meaning in the art. The term "anti-cancer agent" is used synonymously with "chemotherapeutic".

In certain embodiments, the target anti-cancer agent to be screened is selected from the group consisting of PI3-kinase inhibitors, AKT inhibitors, taxanes, antimetabolites, alkylating agents, cell cycle inhibitors, topoisomerase inhibitors and cytotoxic antibodies.

Where the chemotherapeutic agent is a PI3-kinase inhibitor, suitable examples include, but are not limited to, wortmannin, LY294002, demethoxyviridin, IC87114, NVP-BEZ235, BAY 80-6946, BKM120, GDC-0941, GDC-9080; including combinations thereof; and pharmaceutically acceptable salts, solvates, hydrates, stereoisomers, clathrates and prodrugs of any of the above.

Where the target anti-cancer agent is an AKT inhibitor, suitable examples include, but are not limited to, MK-2206, GSK690693, perifosine, PHT-427, AT7867, honokiol, PF-04691502; including combinations thereof; and pharmaceutically acceptable salts, solvates, hydrates, stereoisomers, clathrates and prodrugs of any of the above.

Where the target anti-cancer agent is a taxane, suitable examples include, but are not limited to, paclitaxel and docetaxel; including combinations thereof; and pharmaceutically acceptable salts, solvates, hydrates, stereoisomers, clathrates and prodrugs of any of the above.

Where the target anti-cancer agent is an antimetabolite, suitable examples include, but are not limited to, methotrexate, 5-fluorouracil, capecitabin, cytosinarabinoside (Cytarabin), gemcitabine, 6-thioguanin, pentostatin, azathioprin, 6-mercaptopurin, fludarabin and cladribin; including combinations thereof; and pharmaceutically acceptable salts, solvates, hydrates, stereoisomers, clathrates and prodrugs of any of the above.

Where the target anti-cancer agent is an alkylating agent, suitable examples include, but are not limited to, mechlorethamine, cyclophosphamide, ifosfamide, trofosfamide, melphalan (L-sarcolysin), chlorambucil, hexamethylmelamine, thiotepa, busulfan, carmustine (BCNU), streptozocin (streptozotocin), dacarbazine (DTIC; dimethyltriazenoimidazol ecarboxamide) temozolomide and oxaliplatin; including combinations thereof; and pharmaceutically acceptable salts, solvates, hydrates, stereoisomers, clathrates and prodrugs of any of the above.

Where the target anti-cancer agent is a cell cycle inhibitor, suitable examples include, but are not limited to, Epothilone, Vincristine, Vinblastine, UCN-01, 17AAG, XL844, CHIR-124, PF-00477736, CEP-3891, Flavopiridol, berberine, P276-00, terameprocol, isoflavone daidzein, B12536, B16727, GSK461364, Cyclapolin, ON-01910, NMS-P937, TAK-960, Ispinesib, Monastrol, AZD4877, LY2523355, ARRY-520, MK-0731, SB743921, GSK923295, Lonafarnib, proTAME, Bortezomib, MLN9708, ONX0912, CEP-18770; including combinations thereof; and pharmaceutically acceptable salts, solvates, hydrates, stereoisomers, clathrates and prodrugs of any of the above; particularly suitable examples of cell cycle inhibitors include, but are not limited to, Hespaeradin, ZM447439, VX-680, MLN-8054, PHA-739358, AT-9283, AZD1152, MLN8237, ENMD2076, SU6668; including combinations thereof; and other inhibitors of Aurora kinases; and pharmaceutically acceptable salts, solvates, hydrates, stereoisomers, clathrates and prodrugs of any of the above.

In certain embodiments, the second agent is incubated with the population of cells prior to the addition of the target anti-cancer agent. The target agent may only be administered after a recovery phase, the recovery phase being characterised by a lack of administration of the second agent or the target agent. For example, the population of cells may be administered the second agent in an amount sufficient to increase the level of the expression of OPRK1 and/or BAD by the desired amount prior to the onset of the recovery phase. The recovery phase may be for at least 1 day. Preferably, the recovery phase is from 2 to 7 days. More preferably, the recovery phase is for 2 to 5 days. More preferably, the recovery phase is 3 days. Most preferably, the recovery phase, or incubation with the second agent, is of sufficient time to enable the level of expression of OPRK1 and/or BAD to increase by at least 5%, at least 10%, at least 20%, at least 30%, at least 40%, at least 50%, at least 60%, 70%, at least 80%, at least 90%, or at least 100%, respectively, compared to the normal basal levels expected in the specific cancer cell type prior to addition of the target anti-cancer agent. After the recovery phase, the target agent may then be administered to the population of cells. It is thought that the efficacy of some target agents may be enhanced by the use of a recovery phase as opposed to continuous or concurrent administration, particularly where the agent that enhances the expression of OPRK1 and/or BAD is itself a cytostatic agent. The second agent that is cytostatic will synchronise the phase of the cell cycle within which the cancer cells reside. The recovery period will allow for a temporary reprieve of cytostasis. Without wishing to be bound by theory, it is thought that by synchronising the cancer cells at a particular stage in the cell cycle, the administration of the target anti-cancer agent after the recovery period will act on cells in an aligned state, thereby increasing sensitivity of the cancer cell to a select group of anti-cancer agents. Certain cellular processes that are arrested during cytostasis are desirable for achieving apoptosis, thus continual cytostasis may preclude the greatest enhancement in therapeutic activity of particular target agents from being achieved. Thus, particularly suitable anti-cancer agents to be screened according to the present involve are cell cycle inhibitors.

In another embodiment, the target anti-cancer agent and the second agent are added to the population of cells simultaneously.

In another embodiment, the second agent that increases the expression of OPRK1 and/or BAD is selected from the list consisting of 6-β-naltrexol, methylnaltrexone, or combinations thereof. Preferably, the second agent is 6-β-naltrexol or a pharmaceutically acceptable salt thereof.

As used herein "6-β-naltrexol" refers to 17-(Cyclopropylmethyl)-4,5-epoxymorphinan-3,6beta, 14-triol and pharmaceutically acceptable salts, solvates, hydrates, stereoisomers, clathrates and prodrugs thereof. 6-β-naltrexol is a major active metabolite naltrexone. The term 6-β-naltrexol also encompasses functionally equivalent analogues thereof and metabolites that retain functional equivalence with respect to the novel uses of 6-β-naltrexol embodied within the invention.

In another embodiment, the 6-β-naltrexol is added to a final concentration of at least about 0.34 ng/ml. The 6-β-naltrexol may be added to a final concentration of about from 0.34 ng/ml to about 3,400 ng/ml. Preferably, the 6-β-naltrexol is added to a final concentration of at least about 34 ng·ml to about 3,400 ng/ml. More preferably, the 6-β-naltrexol is added to a final concentration of at least about 340 ng/ml to 3,400 ng/ml.

In invention is further explain with reference to the following non-limiting examples

EXAMPLES

Figure 2A:
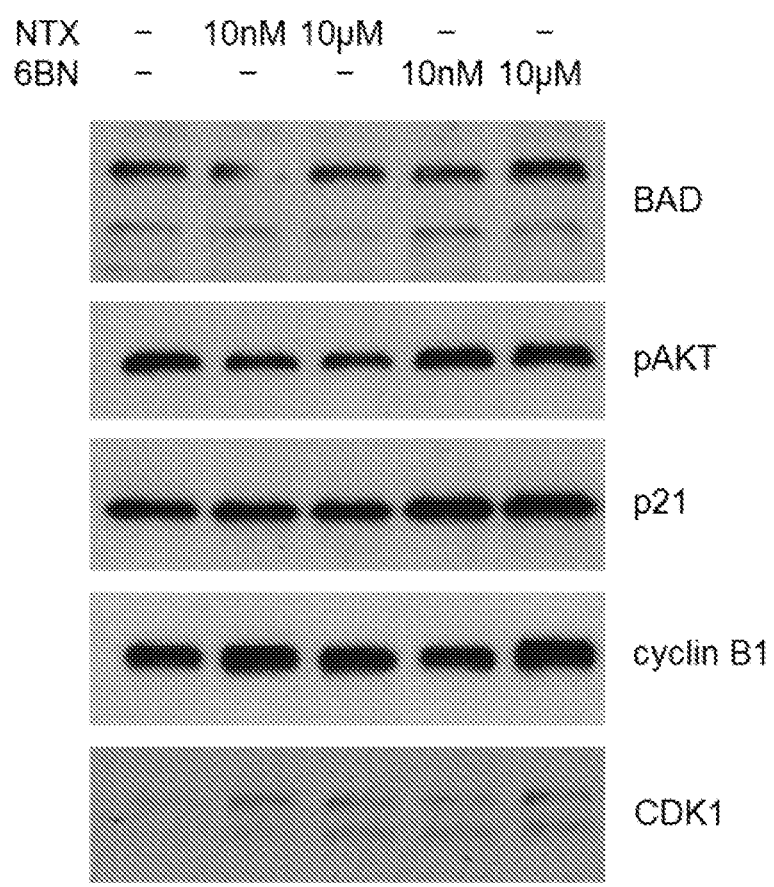
FIG. 2 shows the effect of either 10 nM or 10 µM 6-β-naltrexol or 10 nM or 10 µM naltrexone on the level of expression of BAD, pAKT, p21, cyclin B and CDK1 in HCT116 cells.
Figure 2B:
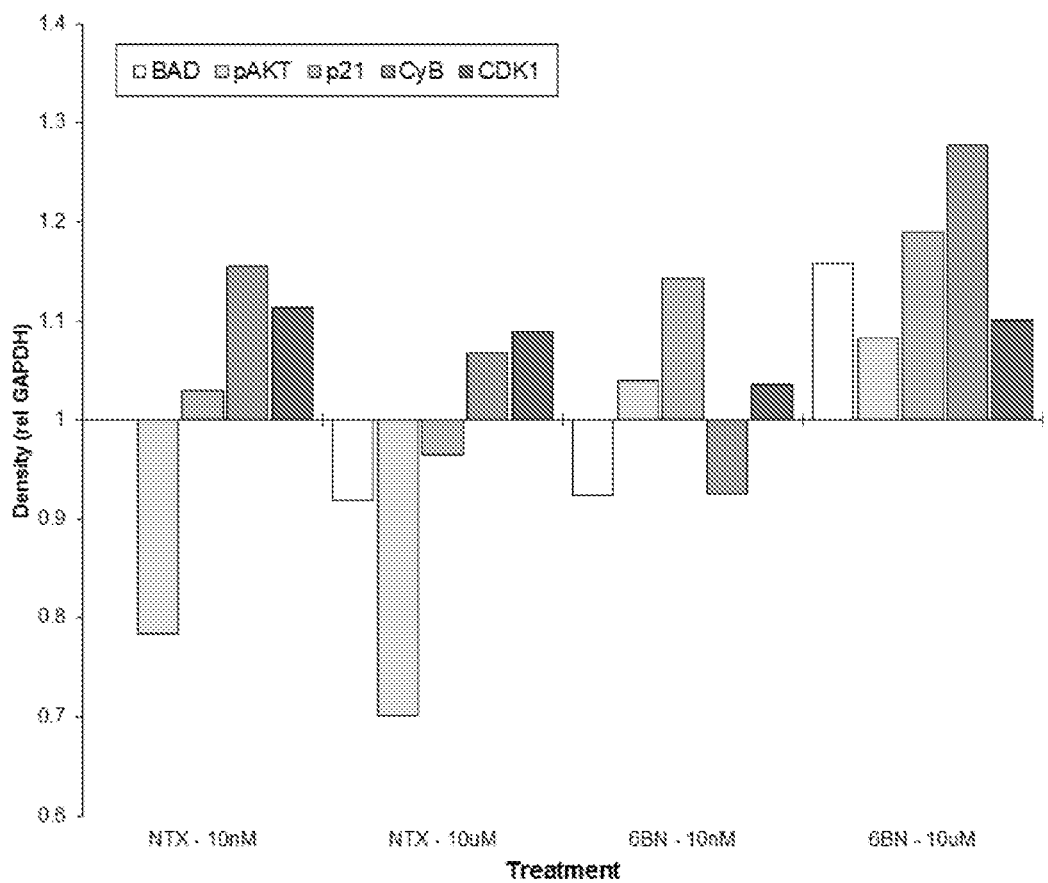
Figure 3:
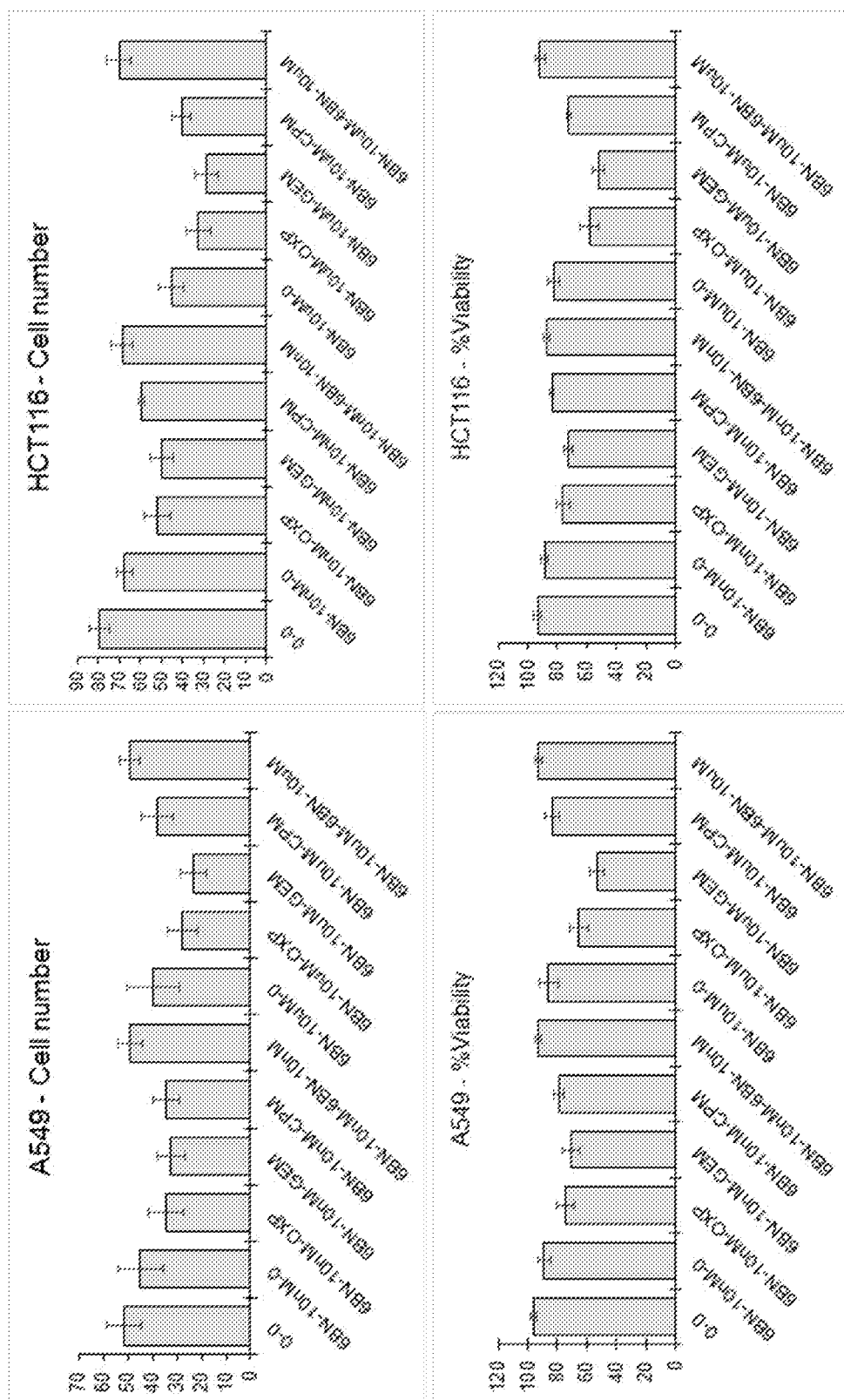
FIG. 3 shows the effect of co-administration of 10 nM or 10 µM 6-β-naltrexol together with cyclophosphamide, gemcitabine, or oxaliplatin on the growth (a and b) and viability (c and d), of A549 lung cancer cells (a and c) and HCT116 colon cancer cells (b and d). Experiments were performed alongside a control where cells were administered either double doses of 10 nM or 10 µM 6-β-naltrexol, or were left untreated (0-0). Columns represent the means and standard deviations of five separate experiments.

Determination of the Level of Expression of OPRK1 and BAD after Administration of 6-β-naltrexol In order to determine the effect of 6-β-naltrexol or naltrexone on the level of expression of OPRK1, A549 lung cancer or HCT116 colon cancer cells were seeded onto 6-well plates at a density of $2 \times 10^5$ cell/well, and allowed to adhere overnight. Cells were then cultured in the presence of naltrexone or 6-β-naltrexol at concentrations of 1 nM, 10 nM, 100 nM, 1 µM or 10 µM for a further 48 h. Cells were then harvested and processed for measurements of OPRK1, opioid receptor-µ1 (OPRM1) and GAPDH using standard immunoblotting techniques. The effect of 6-β-naltrexol or naltrexone on the level of expression of BAD was investigated by using the same protocol as outlined above. The effect was determined in HCT116 cells using either 10 nM or 10 µM of 6-β-naltrexol or 10 nM or 10 µM naltrexone (FIG. 2).

The results show that both naltrexone and 6-β-naltrexol increase the level of expression of ORPK1 in A549 cells, whereas 6-β-naltrexol also increases the level of expression of OPRK1 in HCT116 cells. Naltrexone down-regulates the level of expression of OPRK1 in HCT116 cells. In addition, 10 µM 6-β-naltrexol increases the level of expression of BAD in HCT116 cells by more than 10%, whereas both concentrations of naltrexone and 10 nM 6-β-naltrexol have a negligible effect on the level of expression of BAD.

Increasing the Level of OPRK1 and/or BAD Expression Boosts the Cytotoxicity of Anti-Cancer Agents The impact of combining 6-β-naltrexol with other chemotherapeutic agents was tested by culturing cells according to a treatment schedule that involved two phases of treatment. The first phase involved priming with 10 nM 6-β-naltrexol or 10 μM 6-β-naltrexol for 48 h, before treatment with another drug for a further 48 h. A549 and HCT116 cells were seeded into 6-well plates at a density of $2 \times 10^5$ cells/well and left to adhere overnight. Media was removed after 48 h, and cells were rinsed gently with drug-free medium. Fresh culture medium that contained cyclophosphamide (CPM), gemcitabine (GEM) or oxaliplatin (OXP) was then added to the cells. The concentrations of the chemotherapy agents used were approximately ¼ IC50, as established previously (Liu W M, Fowler D W, Smith P, Dalgleish A G. Pre-treatment with chemotherapy can enhance the antigenicity and immunogenicity of tumours by promoting adaptive immune responses. Br J Cancer. 2010 Jan. 5; 102(1): 115-23). Cells were then left for a further 48 h before assessment of cell number of viability by cell counting using trypan blue dye as a way of discriminating live and dead cells. Cytostasis was indicated by a reduction in cell number and no associated reduction in cell viability.

The experiments show that when 6-β-naltrexol is added in an amount sufficient to raise the level of expression of OPRK1 by at least 10%, the cytotoxic effect of certain anti-cancer agents is increased. This effect is observed in the absence of any independent increase in cytotoxicity caused by the administration of a higher dose of 6-β-naltrexol (FIG. 2). Thus, an agent that increases the expression of OPRK1 is capable of enhancing the therapeutic efficacy of particular anti-cancer agents.

The invention claimed is:

1. An in vitro method for identifying an anti-cancer agent, the therapeutic efficacy of which is enhanced upon administration with a second agent that increases the expression of opioid receptor kappa-1 (OPRK1), comprising the steps of:
   a) co-incubating a population of cells with a target anti-cancer agent and said second agent; and
   b) measuring the cytotoxicity and/or cytostasis in the population of cells;
   wherein the therapeutic efficacy of the target anti-cancer agent is enhanced if the cytotoxicity and/or cytostasis of the target anti-cancer agent is increased compared to a control, and
   wherein the second agent is 6-β-naltrexol or a pharmaceutically acceptable salt thereof and is provided in an amount sufficient to increase the concentration of OPRK1 by at least 10% above the normal basal levels expected in the population of cells.

2. The method of claim 1, further comprising the steps of:
   c) determining whether there is increased cytotoxicity and/or cytostasis compared to a control.

3. The method according to claim 1 or 2, wherein the second agent is incubated with the population of cells prior to the addition of the target anti-cancer agent.

4. The method according to claim 3, wherein the population of cells are incubated with the second agent for a sufficient time to enable the level of expression of OPRK1 to increase by at least 25%.

5. The method according to claim 1 or 2, wherein the target anti-cancer agent and the second agent are administered to the population of cells simultaneously.

6. The method according to claim 1, wherein the second agent is added to a final concentration of at least 0.34 ng/ml.

7. The method according to claim 6, wherein the second agent is added to a final concentration of from 0.34 ng/ml to 3,400 ng/ml.

8. The method according to claim 7, wherein the second agent is added to a final concentration of from 34 ng/ml to 3,400 ng/ml.

9. The method according to claim 8, wherein the second agent is added to a final concentration of from 340 ng/ml to 3,400 ng/ml.

10. The method according to claim 1 or 2, wherein the population of cells are, or are derived from, an immortalized cell line.

11. The method according to claim 1 or 2, wherein the population of cells are, or are derived from, a tumour biopsy obtained from a subject having cancer.

12. The method according to claim 1 or 2, wherein the population of cells are of human origin.

* * * * *